(12) United States Patent
Kileny et al.

(10) Patent No.: US 9,415,181 B2
(45) Date of Patent: Aug. 16, 2016

(54) AMBIDEXTROUS ERGONOMIC FACE MASK

(71) Applicants: The Regents of The University of Michigan, Ann Arbor, MI (US); The Regents of the University of California, Oakland, CA (US)

(72) Inventors: Joel L. Kileny, Ann Arbor, MI (US); Jeffrey Plott, Algonac, MI (US); Albert J. Shih, Ann Arbor, MI (US); Lance Patak, Ann Arbor, MI (US); Kevin Tremper, Ann Arbor, MI (US); Daniel Edward Lee, San Deigo, CA (US)

(73) Assignees: The Regents of the University of Michigan, Ann Arbor, MI (US); The Regents of the University of California, Oakland, CA (US)

( * ) Notice: Subject to any disclaimer, the term of this patent is extended or adjusted under 35 U.S.C. 154(b) by 278 days.

(21) Appl. No.: 14/071,881

(22) Filed: Nov. 5, 2013

(65) Prior Publication Data
US 2014/0128678 A1    May 8, 2014

Related U.S. Application Data

(60) Provisional application No. 61/722,773, filed on Nov. 5, 2012.

(51) Int. Cl.
| | |
|---|---|
| *A61M 16/06* | (2006.01) |
| *A61B 1/00* | (2006.01) |
| *A61M 16/04* | (2006.01) |
| *A61M 16/08* | (2006.01) |
| *A61B 1/267* | (2006.01) |

(52) U.S. Cl.
CPC ............ *A61M 16/06* (2013.01); *A61B 1/00154* (2013.01); *A61B 1/00165* (2013.01); *A61M 16/0488* (2013.01); *A61M 16/0816* (2013.01); *A61B 1/267* (2013.01)

(58) Field of Classification Search
CPC ............ A61M 16/06; A61M 16/0816; A61M 16/0606
USPC ............. 128/200.26, 206.26, 205.25, 206.21, 128/206.23, 206.24, 206.28
See application file for complete search history.

(56) References Cited

U.S. PATENT DOCUMENTS

| 4,580,556 A * | 4/1986 | Kondur .................. A61B 1/267 128/206.28 |
| 8,393,324 B1 * | 3/2013 | Saad ..................... A61M 16/06 128/205.13 |

(Continued)

*Primary Examiner* — Jason Flick
*Assistant Examiner* — Margaret Luarca
(74) *Attorney, Agent, or Firm* — Reising Ethington P.C.

(57) ABSTRACT

A face mask that may be used for bag-mask ventilation, during the induction of general anesthesia for example, and allows for two-handed or ambidextrous use. The face mask includes a dome connected to a deformable rim, which forms an enclosed air space when the rim is pressed against a patient's face. The dome has a connection port and a contoured outer surface adjacent the connection port. The contoured outer surface includes contour features such as a pair of crossed composite recesses which may each receive a different one of a user's thumbs. The connection port is aligned with the patient's mouth when the mask is in use and an adapter may be included that attaches to the connection port and provides a ventilation port as well as an intubation port that is aligned with the mouth.

22 Claims, 10 Drawing Sheets

(56) References Cited

U.S. PATENT DOCUMENTS

| | | | |
|---|---|---|---|
| 2002/0108610 A1* | 8/2002 | Christopher | A61M 16/04 128/200.26 |
| 2003/0172932 A1* | 9/2003 | Matioc | A61M 16/06 128/206.24 |
| 2005/0139220 A1* | 6/2005 | Christopher | A61M 16/04 128/207.14 |
| 2007/0251528 A1* | 11/2007 | Seitz | A61M 16/06 128/205.25 |
| 2014/0230821 A1* | 8/2014 | Warters | A61M 16/06 128/205.25 |

* cited by examiner

AMBIDEXTROUS ERGONOMIC FACE MASK

CROSS-REFERENCE TO RELATED APPLICATION

This application claims the benefit of U.S. Provisional Ser. No. 61/722,773 filed on Nov. 5, 2012, the entire contents of which are hereby incorporated by reference.

TECHNICAL FIELD

This invention relates generally to face masks used for bag-mask ventilation, which are often employed during the induction of general anesthesia.

BACKGROUND

Face mask ventilation, or bag-valve-mask ventilation, is a routine procedure which allows for oxygenation and ventilation of patients by ensuring proper airway patency. Effective mask ventilation has two requirements. First, airway patency must be established. Second, leakage between the patient's face and the mask must be eliminated.

Difficult mask ventilation, which often results from an inadequate seal between the patient's face and the mask, poses significant challenges, particularly to anesthesiologists. The patient's safety hinges upon proper ventilation and oxygenation during anesthesia. Recent studies have found an approximately 5-8% incidence of difficult mask ventilation. Various predictors of difficult mask ventilation include patients that have a thick or obese neck, edentulous dentition, facial hair, sleep apnea, and those patients that snore or are obese. Particular facial features can also result in difficult mask ventilation, including a prominent nose, a narrow facial structure, and hollow cheeks.

Another important consideration regarding mask ventilation is its effect on the clinician performing the procedure. When prolonged mask ventilation is required, the clinician's hand that holds the mask can tire easily for two reasons. First, the hand must apply increased pressure on the mask in order to achieve a tight seal. An additional pair of hands may be required to press the mask against the patient's face to facilitate ventilation. Second, the mask has an abnormal shape that the clinician's hand must conform to in order to establish a reliable and steady grip. These factors which lead to fatigue can be exacerbated by the predictors of difficult mask ventilation as described above. Additionally, clinicians with small hands have to work harder to achieve adequate seal and ventilation. This can be attributed to the distance between the thumb, which sits on the dome of the mask, and the little finger, which rests on the posterior angle of the patient's mandible. Improving the mask structure in order to achieve a tight seal with less effort allows anesthesiologists to focus more on maintaining airway patency. This ultimately will result in better mask ventilation and a decreased risk to patients' safety during anesthesia.

Adapting masks to facilitate a better seal is generally known, as shown in WO 97/07847 which discloses an anesthesia mask with finger grips which protrude from the dome of the mask and guide the placement of the thumb and index finger. U.S. Pat. No. 6,651,661 discloses an anesthesia mask that is ergonomically defined with a left/right asymmetrical design that accommodates holding the mask to the patient's face with the left hand.

SUMMARY

According to one embodiment, there is provided a face mask comprising a deformable rim for engaging and forming a seal between the rim and a patient's face when the rim is pressed against the patient's face in position over the mouth and nose. The face mask has a dome connected to the rim which forms an enclosed air space when the rim is pressed against the patient's face. The dome has a connection port and a contoured outer surface adjacent the connection port. The contoured outer surface has a pair of crossed composite recesses, each of which includes a digit cavity and a thenar eminence cavity aligned with the digit cavity such that the composite recesses are each contoured to receive a different one of a user's thumbs.

According to another embodiment, there is provided a face mask comprising a deformable rim for engaging and forming a seal between the rim and a patient's face when the rim is pressed against the patient's face in position over the mouth and nose. The face mask also includes a dome connected to the rim which forms an enclosed air space when the rim is in position on the patient's face. The dome has a connection port and a contoured outer surface adjacent the connection port. There is also provided an adapter having an intubation port and a ventilation port. The adapter may attach to the connection port of the face mask such that the connection port and the intubation port of the adapter extend along a common axis and the ventilation port extends along an angled axis relative to the common axis.

Also provided is a face mask kit comprising a face mask according to one or more of the embodiments identified herein along with a separate adapter attachable to the connection port of the face mask, the adapter having an intubation port and a ventilation port.

BRIEF DESCRIPTION OF THE DRAWINGS

Preferred exemplary embodiments will hereinafter be described in conjunction with the appended drawings, wherein like designations denote like elements, and wherein.

DETAILED DESCRIPTION OF THE ILLUSTRATED EMBODIMENTS

The face mask disclosed herein provides a contoured design that assists the clinician in use of the mask, accommodating both left- and right-handed holding of the mask as well as assisting clinicians with smaller hands that might otherwise not be large enough to both hold the mask in place and extend his or her fingers around the patient's mandible in accordance with proper ventilation technique. The disclosed mask could also be of beneficial use in cases where proper ventilation may be inhibited by the patient's facial structure or other features such as edentulous dentition or facial hair. In such situations when mask ventilation can be difficult, an additional pair of hands may be required to facilitate the procedure and ensure the patient's safety. Accordingly, the face mask disclosed herein includes a contoured outer surface that accommodates ambidextrous use as well as two-handedness in a manner that may involve less muscle fatigue to maintain a seal against the patient's face than is required using prior art face masks. The contoured dome can allow the clinician's hand to be efficient and not waste muscle energy on movement or finger positions that will increase fatigue while attempting to improve mask ventilation. The clinician could thus do less work to create the same or improved seal between the mask and the patient's face. The contour features of the disclosed mask can allow the hand muscles to perform their normal, natural mechanism of action, avoiding the use of muscles, such as forearm flexors and extensors, that should not be primarily responsible for creating the seal. These contour features can also help the clinician avoid flexion of the wrist, another unnatural movement of the upper extremity that contributes to fatigue.

Figure 1:
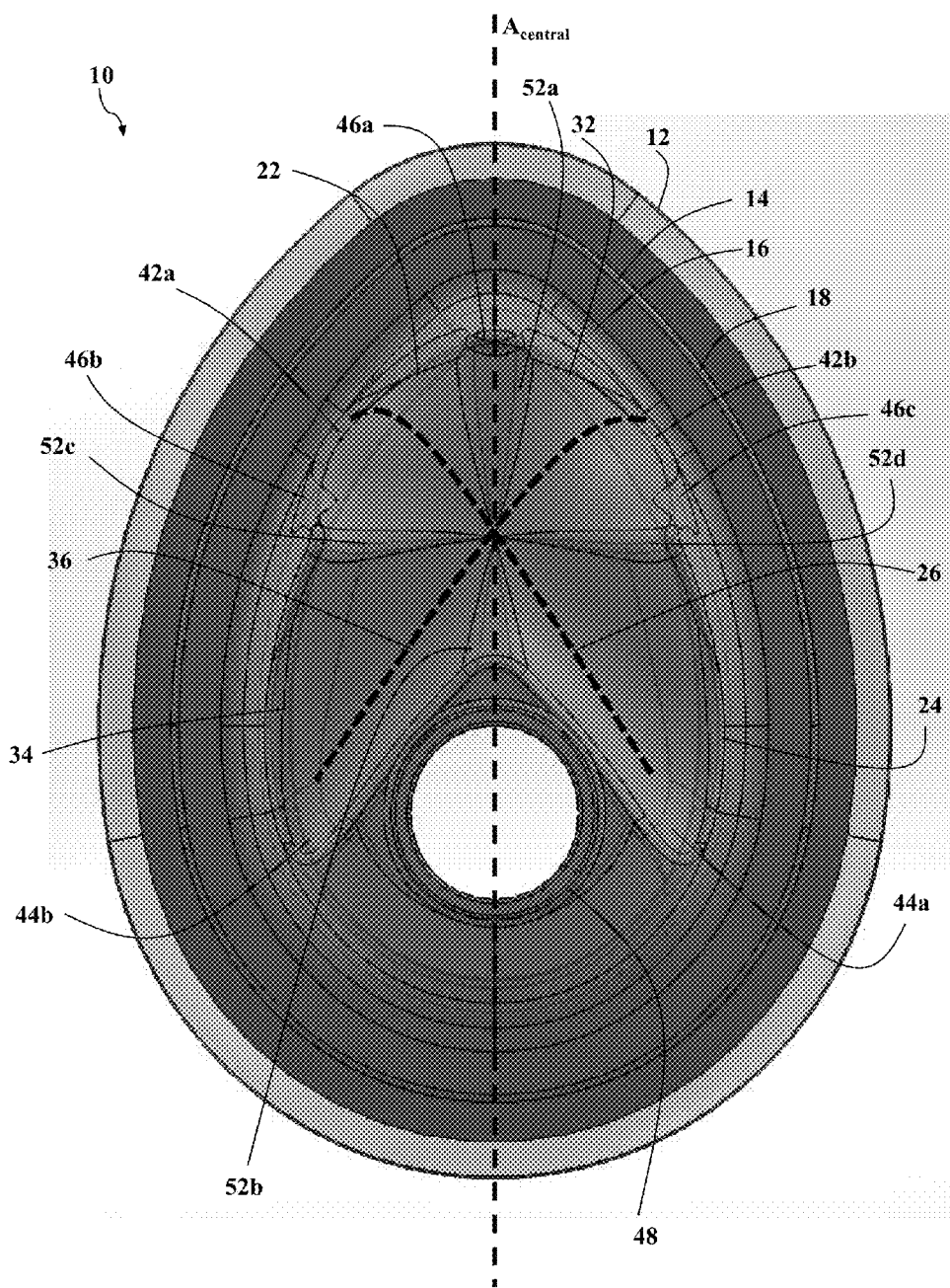
FIG. 1 is an elevational view of an embodiment of a face mask constructed in accordance with the present invention.
Figure 2:
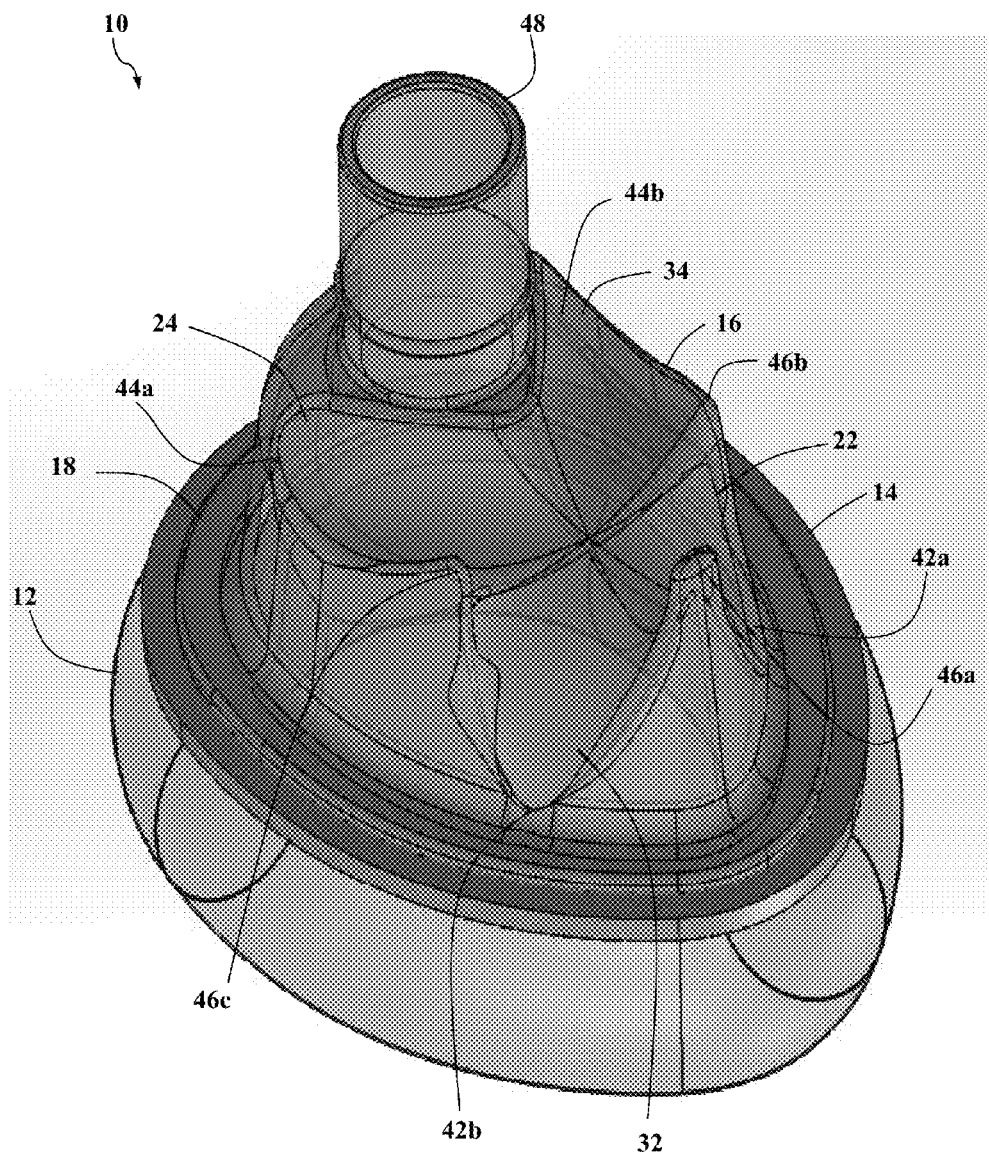
FIG. 2 is a perspective view of the embodiment of the face mask depicted in FIG. 1.

As shown in FIG. 1 and FIG. 2, an illustrative face mask 10 comprises a deformable rim 12 coupled to a dome 14. The dome 14 has a contoured outer surface 16 that will be explained in more detail below. The rim 12 makes contact with the patient's face and forms a seal to the patient's face when the rim is pressed against the face in position over the nose and mouth. In this particular embodiment, the rim 12 is made of a soft plastic and inflated. Such a high volume, low-pressure, inflatable, cuffed rim 12 assists in establishing a temporary mold to the patient's face. The rim can be directly connected to the dome or indirectly connected via one or more other components of the mask. As will be apparent to one having ordinary skill in the art, plastics and other materials can be used for the rim 12, such as a soft foam or another deformable material that is capable of at least partially molding with the patient's face. The rim 12 defines a plane constituting the lower boundary of the face mask, and the molding and sealing of the flat plane of the rim 12 on an irregular face contour typically does not closely match, especially in circumstances when the patient has facial deformities or dentures. Ultimately, this can lead to leaks during oxygenation of the patient by mask ventilation.

In order to remedy the potential leakage during ventilation, a clinician applies positive manual pressure on the mask 10 against the patient's face in order to counteract any potential leakage. To achieve this goal, the clinician's thumb and forefinger rest on the dome 14 while the other fingers wrap around the rim 12 and the patient's mandible to lift up on mandibular tissues and assist in sustaining airway patency. This requires hand and forearm muscle force on gripping the dome 14 of the mask 10 with the thumb and index finger, stretching the little finger to reach the angle of the mandible, and applying pressure to the side opposite the hand to achieve an effective seal. To minimize clinician fatigue during this process, the mask 10 provides a dome 14 with a contoured outer surface 16 and a peripheral border 18. The dome 14 in the illustrated embodiment is made from transparent PVC which provides strength and allows the clinician to monitor the patient's mouth; however, other suitable materials for the dome will be apparent to one having ordinary skill in the art. In this particular embodiment, the height of the dome 14 is decreased in comparison with traditional face masks to decrease the stretch and muscle effort needed to maintain both a grip on the mask 10 with the index finger and the placement of the little finger underneath the angle of the mandible. When the rim 12 is in position against the patient's face, the dome 14 and rim 12 together form an enclosed air space.

During ventilation, the clinician's thumb can rest on the contoured outer surface 16 of the dome 14 which can accommodate the natural curvature of the thumb and thenar eminence. Particularly, the contoured outer surface 16 has a right thenar eminence cavity 22 and a right digit cavity 24 which together form a composite recess 26. To allow for ambidextrous and/or two-handed use, the depicted mask 10 also has a left thenar eminence cavity 32 and a left digit cavity 34 which together form a composite recess 36. Crossed composite recesses 26, 36 are represented generally by the curved dotted lines in FIG. 1. Between the cavities, there are ridges 52 extending generally upwards from a plane defined by the deformable rim. More specifically, ridge 52a is formed between the right thenar eminence cavity 22 and the left thenar eminence cavity 32. Ridge 52b is formed between the right digit cavity 24 and the left digit cavity 34. Ridge 52c is formed between the right thenar eminence cavity 22 and the left digit cavity 34, and finally, ridge 52d is formed between the left thenar eminence cavity 32 and the right digit cavity 24.

To allow for ambidextrous use, the clinician's thumb will span the crossed composite recesses 26 or 36 depending on which hand is used. This intersection coincides with the transition between the right digit cavity 22 and the right thenar eminence cavity 24, as well as the left digit cavity 32 and the left thenar eminence cavity 34, respectively. The intersection also generally coincides with a central axis $A_{central}$ of the mask 10. When a single clinician is applying pressure with his or her right hand to the mask for ventilation, for example, his or her thumb can span the composite recess 26 and his or her index finger may wrap around a connection port 48 and rest on peripheral border 18. Similarly, when a single clinician is applying pressure with his or her left hand to the mask for ventilation, for example, his or her thumb can span the composite recess 36 and his or her index finger can rest on peripheral border 18.

As shown in FIG. 1, the right thenar eminence cavity 22 and the left thenar eminence cavity 32 are bilateral with respect to the central axis $A_{central}$, and the right digit cavity 24 and the left digit cavity 34 are bilateral with respect to the central axis $A_{central}$. Thus, the composite recesses 26, 36 intersect each other such that the thenar eminence cavities 22, 32 are bilaterally positioned relative to each other and the digit cavities 24, 34 are bilaterally positioned relative to each other. Depicted more distinctly in FIG. 2, the composite recess 26 has a proximal end 42a and a distal end 44a. Similarly, the composite recess 36 has a proximal end 42b and a distal end 44b. In the illustrated embodiment, the proximal end 42 is lower than the distal end 44 relative to a plane defined by the deformable rim 12. These ergonometric features mimic the anatomical position of the human hand at rest while standing upright.

As shown more clearly in FIG. 2, the contoured outer surface 16 has three protuberances 46a. 46b. 46c. One protuberance 46a is formed between the thenar eminence cavities 22, 32. A second protuberance 46b is formed between the right thenar eminence cavity 22 and the left digit cavity 34. A third protuberance 46c is formed between the left thenar eminence cavity 32 and the right digit cavity 24. The protuberances 46b. 46c provide fulcrums that can be used to generate strategic forces used to improve the seal. The protuberance 46a extends upwardly from ridge 52a relative to the plane of the rim 12.

The connection port 48 is disposed between the right digit cavity 24 and the left digit cavity 34 such that the connection port 48 is aligned with the central axis $A_{central}$ of the face mask. The face mask 10 is thus bilaterally symmetrical. As shown in FIG. 2, the connection port 48 is a hollow tubular extension arising from the dome 14. The connection port 48 allows for the connection of ventilator tubing or an AMBU (artificial manual breathing unit) bag, either of which provide a source of air or oxygen and a method for assisting the patient with breathing. The connection port 48 can also be situated in a more distal position, thereby allowing more room for composite recess 26 and composite recess 36.

Figure 3:
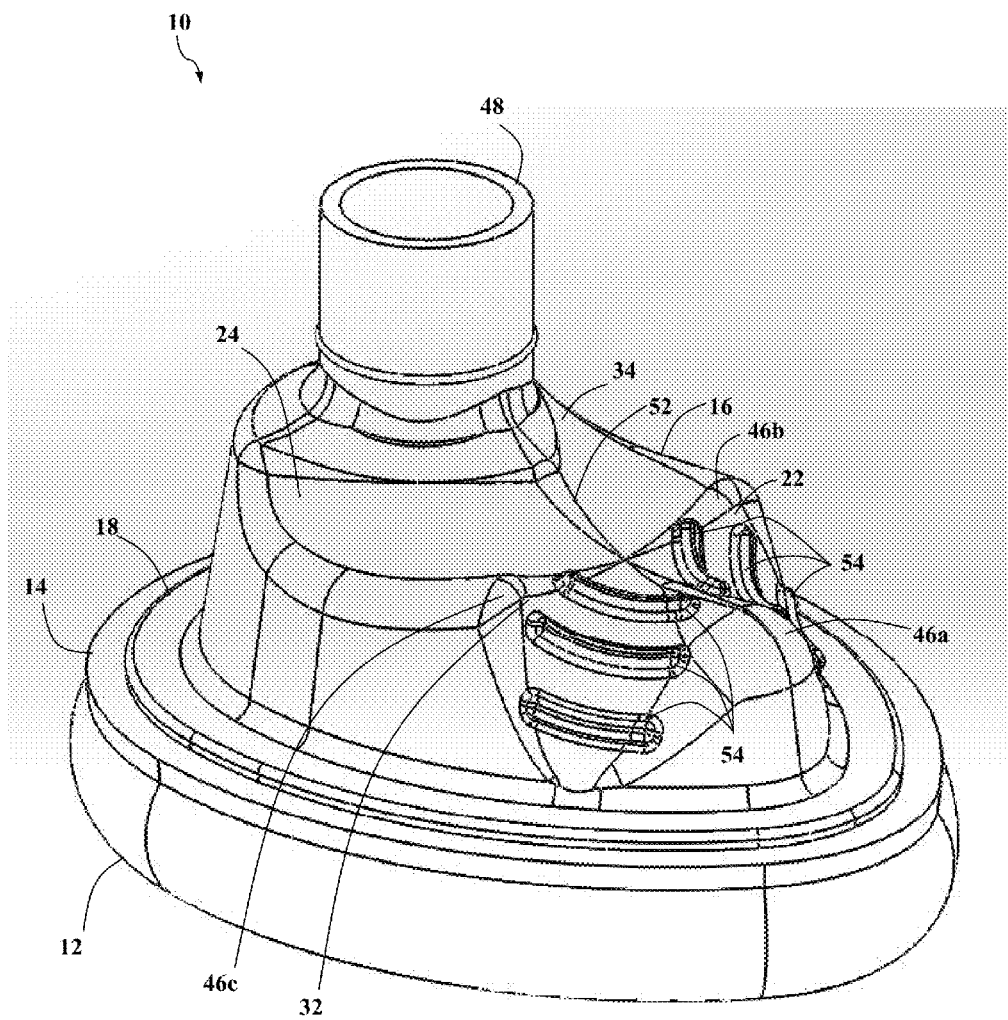
FIG. 3 is a perspective view of another embodiment of the face mask constructed in accordance with the present invention.
Figure 4:
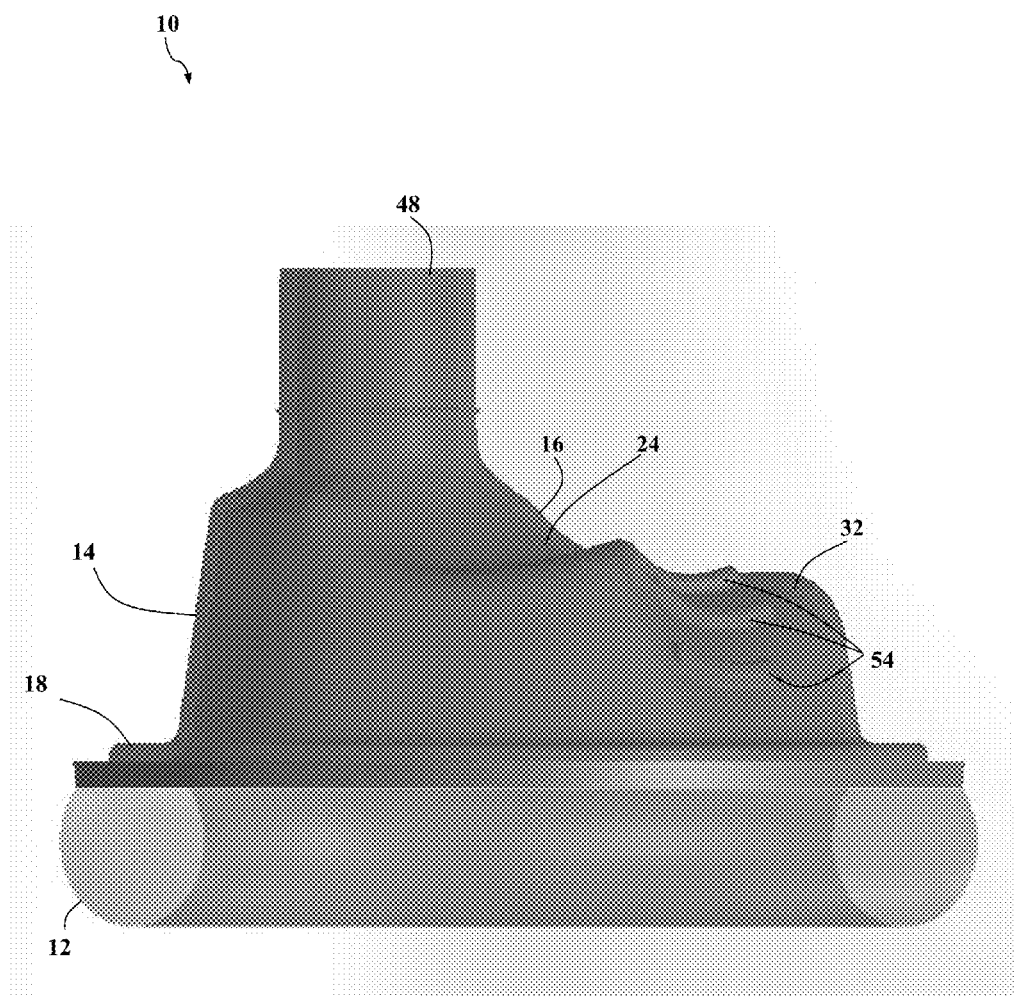
FIG. 4 is a side view of the embodiment of the face mask depicted in FIG. 3.
Figure 5:
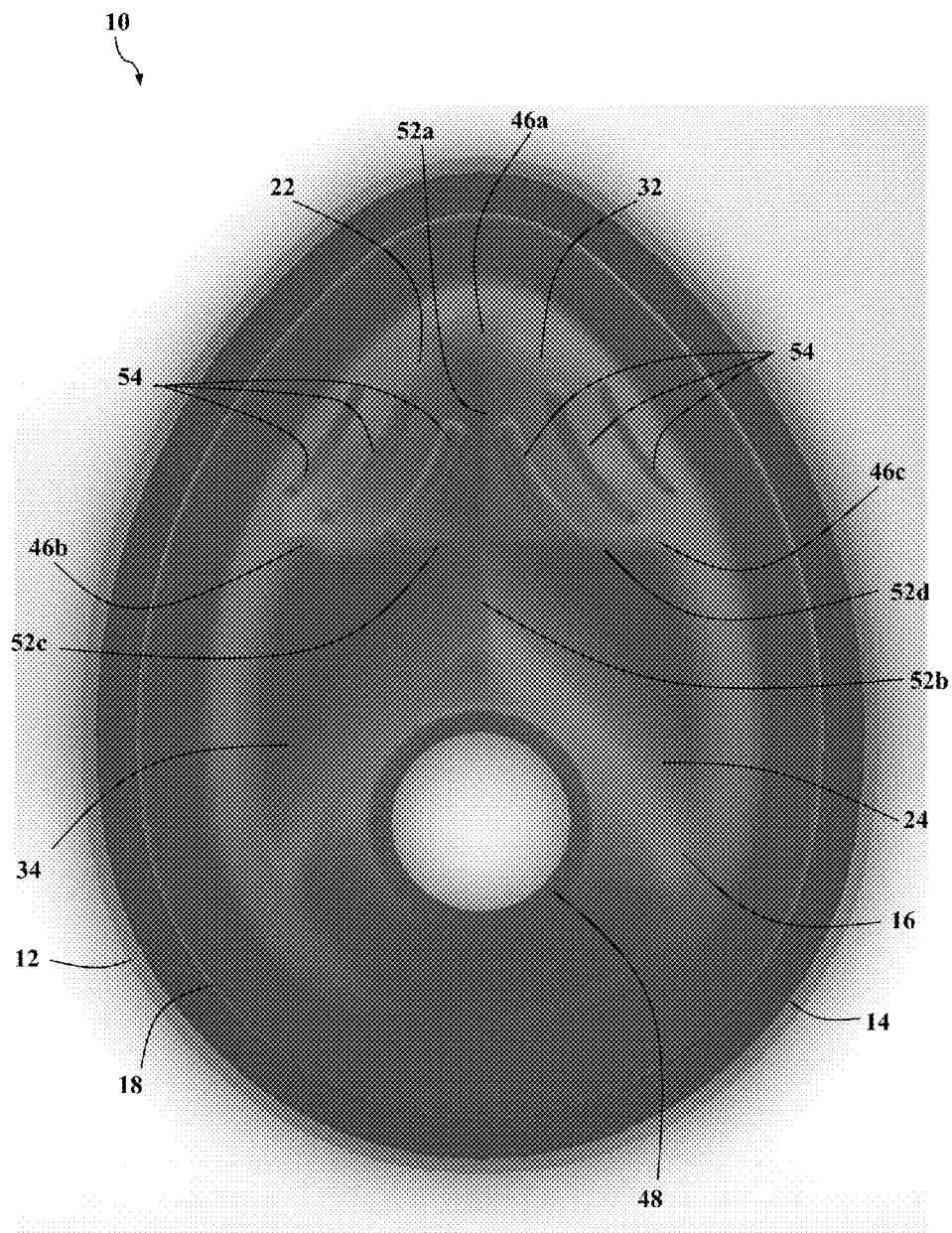
FIG. 5 is an elevational view of the face mask depicted in FIG. 3 and FIG. 4.

A modified embodiment of the face mask 10 is depicted in FIGS. 3-5. As shown therein, the face mask 10 has a rim 12 and a dome 14 that has a contoured surface 16. The contoured surface 16 has a right thenar eminence cavity 22, a right digit cavity 24, a left thenar eminence cavity 32, and a left digit cavity 34. As shown in FIG. 3 and FIG. 4, the left thenar eminence cavity 32 and the right thenar eminence cavity 22 have ribs 54. The ribs 54 can assist in guiding the clinician's thumb so it lies perpendicular to the axis of the patient's face. Furthermore, the ribs 54 can provide traction and thereby allow for easier application of contralateral pressure with the clinician's thumb. Accordingly, the efficacy of the seal on the patient's face may be improved. The mask 10 also has protuberances 46a, 46b, 46c as well as ridges 52a, 52b, 52c, 52d as shown in FIG. 5. In this particular embodiment, the protuberance 46a is located lower than the ridge 52b that extends between the digit cavities 24, 34 with relation to the plane defined by the deformable rim 12.

Figure 6:
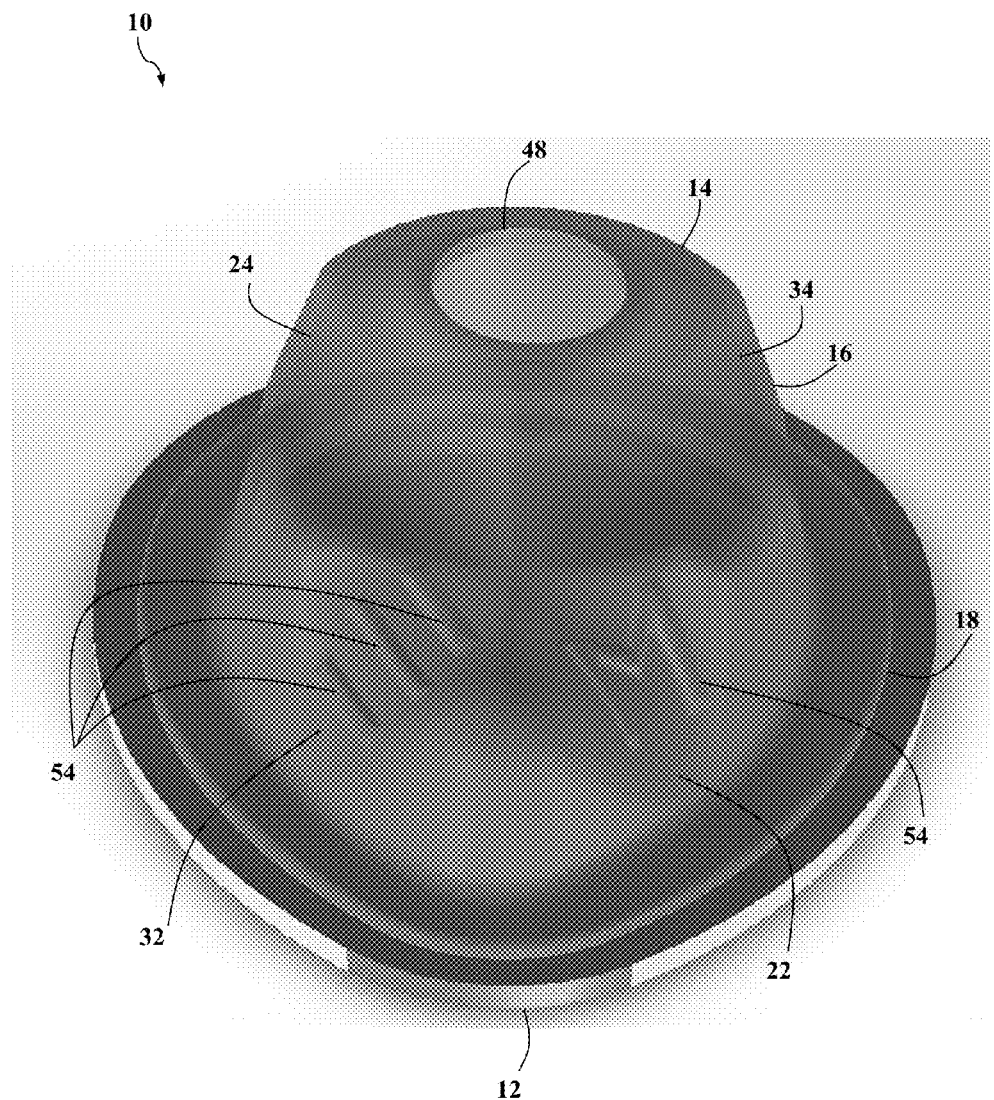
FIG. 6 is an elevational view of another embodiment of the face mask constructed in accordance with the present invention.
Figure 7:
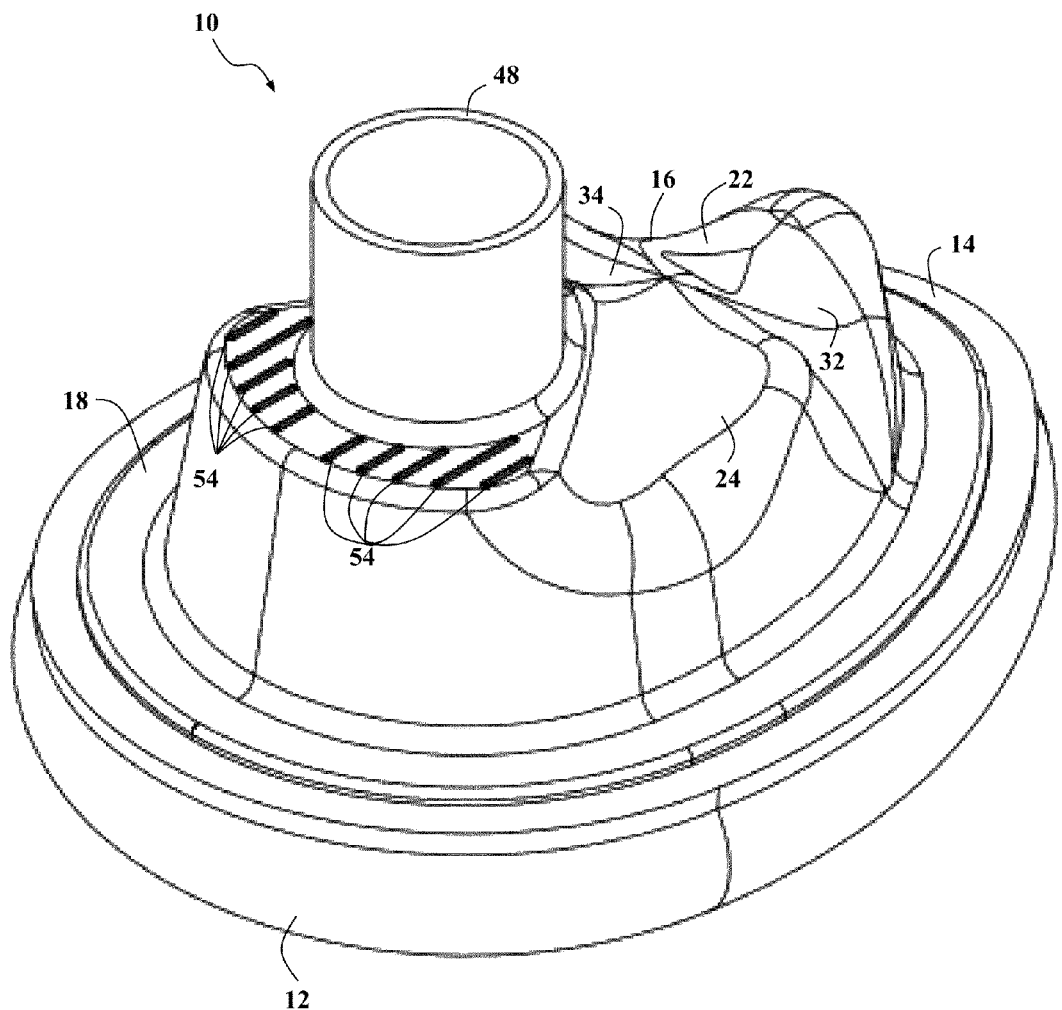
FIG. 7 is a perspective view of an embodiment of a face mask constructed in accordance with the present invention.

FIGS. 6 and 7 show varying positions for the ribs 54. Similar to the other illustrated embodiments, face mask 10 has a right thenar eminence cavity 22, a right digit cavity 24, a left thenar eminence cavity 32, and a left digit cavity 34. In FIG. 6, the mask 10 has three ribs 54 disposed in the left thenar eminence cavity 32. The mask 10 has another rib 54 disposed in the right thenar eminence cavity 22. In FIG. 7, the ribs 54 are located in an area to provide traction for a clinician's thumb when the mask is in use. The ribs 54 of FIG. 7 are designed such that when two clinicians are using the mask, their respective thumbs may be adequately supported. For example, when two clinicians are using the illustrated face mask, it is possible for one clinician's thumb to rest across thenar eminence cavity 22 and digit cavity 34 such that the tip of the clinician's thumb rests upon the area with ribs 54. The other thumb may then rest across thenar eminence cavity 32 and digit cavity 24 such that the tip of that other clinician's thumb also rests upon the area with ribs 54. Thus, the ribs 54 can aid the clinicians in proper hand and finger positioning, provide traction, and thereby increase the efficacy of sealing the mask 10 to the patient's face during ventilation procedures. It should be understood that the ribs may be positioned to facilitate both index finger and thumb support, or may also be located to support single-handed use as opposed to ambidextrous use. Further, the ribs need not be formed into the contoured surface of the mask itself. Rather, the ribs may be of a different material and then glued or otherwise attached to the contoured surface.

Figure 8:
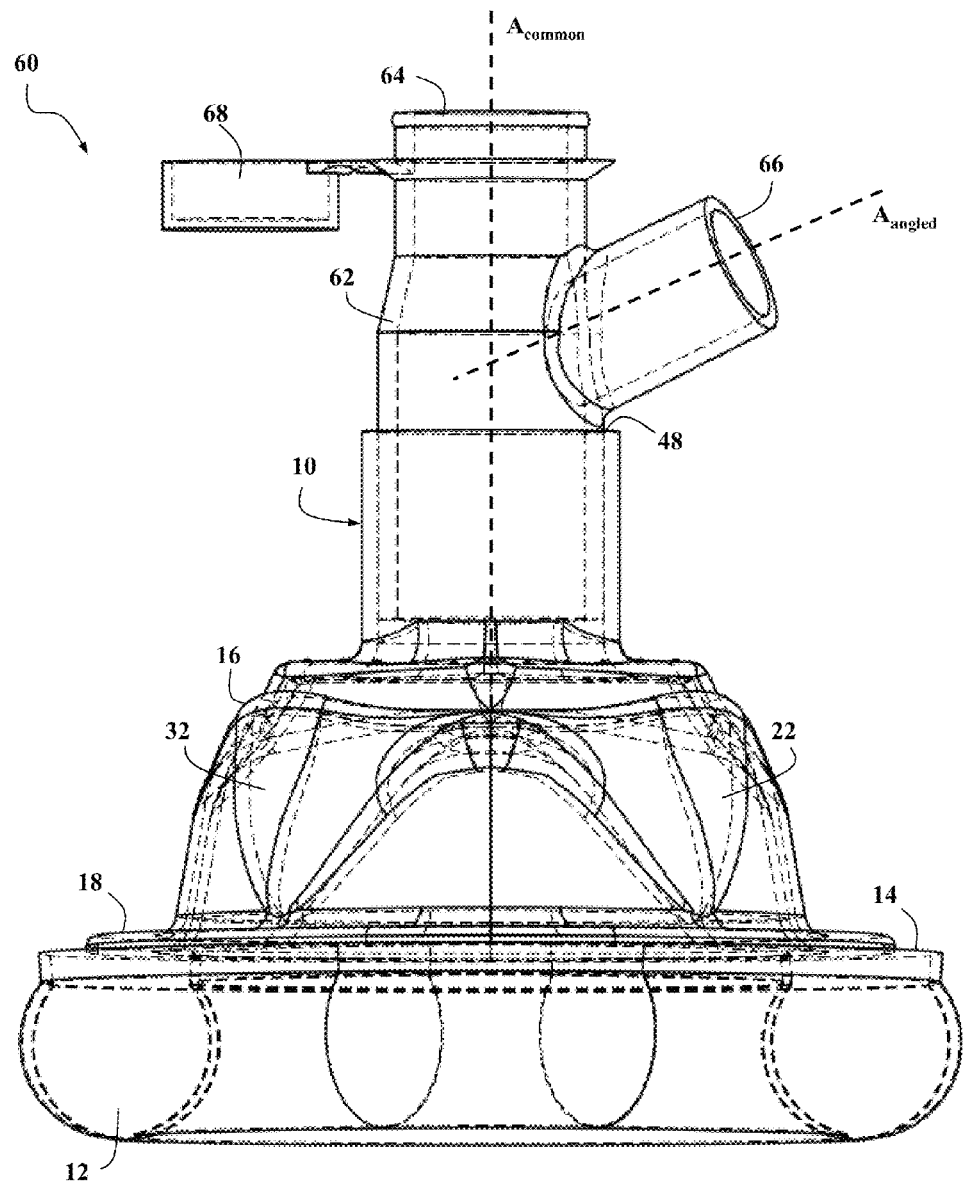
FIG. 8 is a side view of an assembled face mask kit.

FIG. 8 shows an assembled face mask kit 60 that includes face mask 10 and an adapter 62 connected over the connection port 48. The adapter 62 includes an intubation port 64 and a ventilation port 66, and may be removable such that the face mask 10 and adapter 62 may be supplied together in common (or separate) packaging as a kit. In the illustrated embodiment, adapter 62 slides into the connection port 48, but other means of attachment are certainly possible. For example, either the connection port or the adapter may be threaded, include grooves, channels, retaining rings, or other coupling mechanisms. In other embodiments, the adapter may be a unitary part of the connection port 48 formed simultaneously with the dome 14 as a part of the molding or other manufacturing process for the dome. The adapter 62 is attached to the connection port such that the intubation port 64 extends along a common axis $A_{common}$ with the connection port 48. Ventilation port 66 extends along an angled axis $A_{angled}$, which is angled relative to the common axis $A_{common}$. When the mask is being used on a patient, the common axis $A_{common}$ is aligned with a central portion of the patient's mouth when the rim 12 is pressed in position over the mouth and nose. The adapter may also include a closure 68 that may be used to seal the intubation port if only ventilation procedures are being employed. The closure 68 is shown attached by a ring over the intubation port, and can be an integral or separate component. Adapter 62 may be made from a material similar to the material used for the dome 14, such as PVC or another similar plastic.

Figure 9:
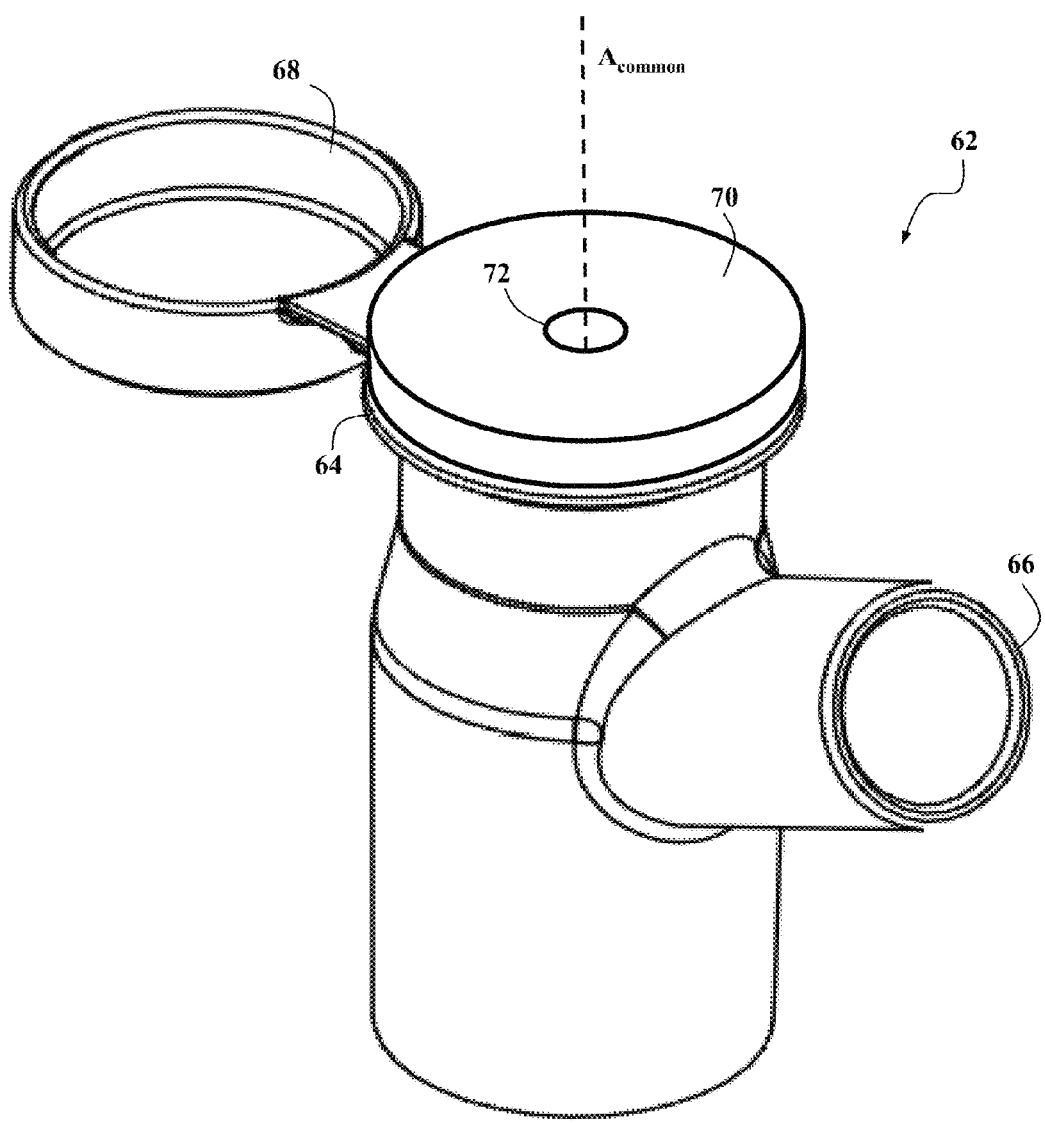
FIG. 9 is an isometric view of an adapter and sealing sleeve that may be used for the face mask kit shown in FIG. 8.
Figure 10:
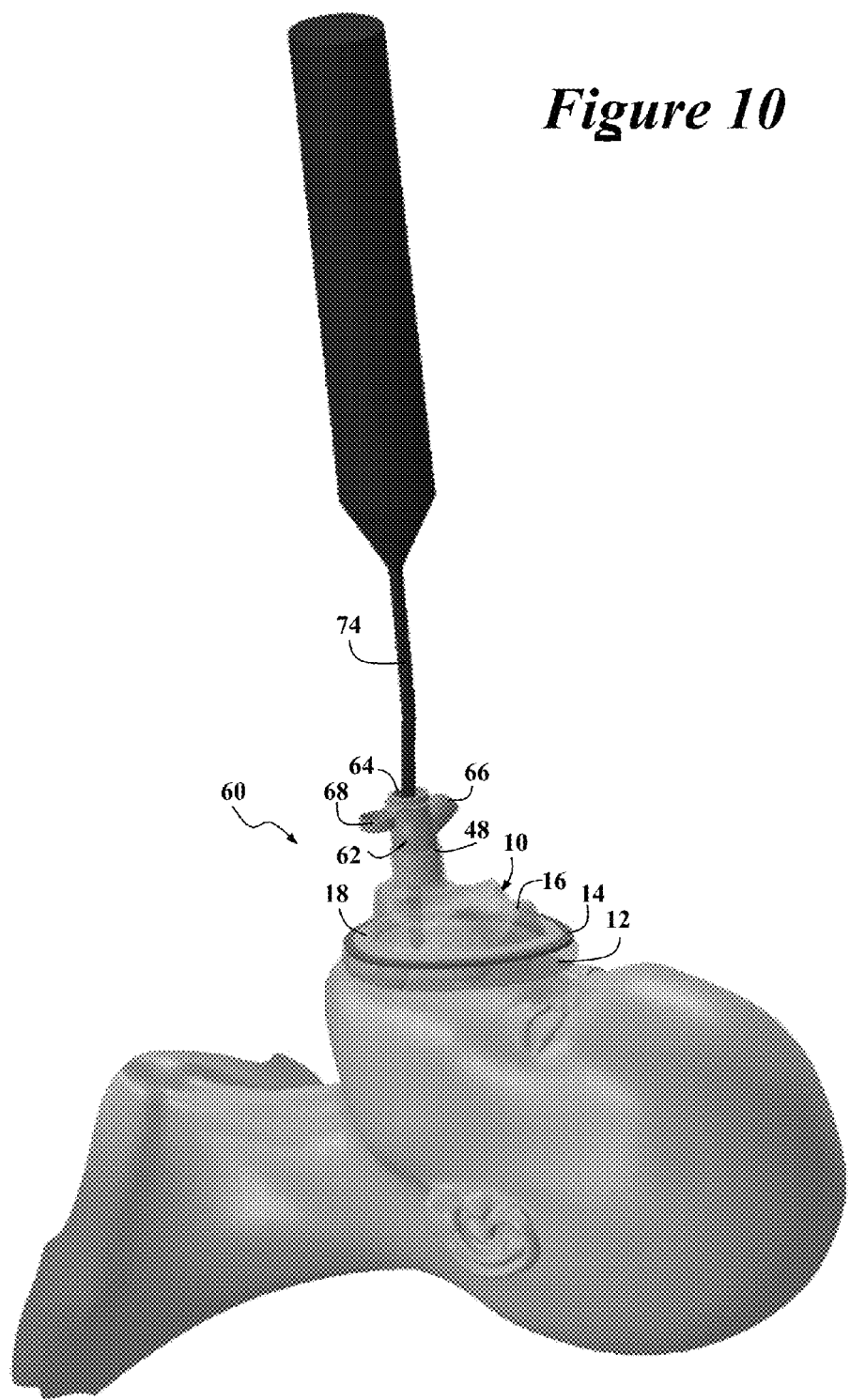
FIG. 10 illustrates an exemplary face mask being used on a patient and accommodating fiber-optic intubation.

Adapter 62 may facilitate the use of fiber-optic intubation through the intubation port 64. As shown in the enlarged view of the adapter 62 in FIG. 9, a sealing sleeve 70 may be attached to the adapter 62, and an opening 72 may accommodate a fiber-optic scope, an endotracheal tube, or both a fiber-optic scope and an endotracheal tube. An illustration of such a procedure is depicted in FIG. 10, where a tube 74 is inserted into the intubation port 64 of the adapter 62, through the connection port 48 of the mask 10 and into the patient's mouth. The tube 74 may be representative of a fiber-optic intubation tube or an endotracheal tube. With reference to FIG. 9, the sealing sleeve 70 may be made from a polymeric material such as rubber or silicone. The elastomeric nature of the sealing sleeve in this particular embodiment facilitates its attachment over the intubation port; however, other methods of attachment will be apparent to one having ordinary skill in the art. The sealing sleeve 70 may have any suitable form, such as a cap as shown in FIG. 9 with the central opening 72 into which the scope or other tube is inserted with a friction fit. As with the closure cap 68, the sealing sleeve 70 may be a separate component or integral with the adapter and, for example, may be attached by a flexible ring as is shown for the closure cap 68.

An advantage of the adapter is that it may be used to provide positive pressure to the patient's airways during intubation. In an asleep patient, positive pressure ventilation in the presence of a sealed system will generate some pressure in the oral cavity whereby the oral cavity anatomy may separate from itself enabling the clinician to more easily pass and visualize the anatomy while performing a fiber-optic procedure. In contrast, without positive pressure, the oral cavity anatomy of an asleep patient is relaxed; and, even with a specialized oral airway device, the anatomy is still collapsed on itself making visualization more difficult. In an awake patient, the mask can be secured to the patient with straps that connect to spikes that arise from a circular ring (not shown) around the connecting port such that the patient receive 100% oxygen during the awake intubation. In the event the patient does not do well or becomes apneic (stops breathing) during the awake procedure because of the sedation medications being used, the patient will have oxygen reserve that will make it safer for the patient.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A face mask, comprising:
    a deformable rim for engaging and forming a seal between the rim and a patient's face when the rim is pressed against the patients face in position over the mouth and nose; and
    a dome connected to the rim and forming an enclosed air space when the rim is pressed against the patient's face, the dome having a connection port and a contoured outer surface adjacent the connection port, the contoured outer surface having a pair of crossed composite recesses that intersect each other along a central axis ($A_{central}$) that passes through a central region of the dome, wherein each composite recess includes a digit cavity and a thenar eminence cavity aligned with the digit cavity such that the composite recesses are each contoured to receive a different one of a user's thumbs.

2. A face mask as defined in claim 1, wherein the composite recesses cross each other at a location between the digit cavity and thenar eminence cavity of each composite recess.

3. A face mask as defined in claim 1, wherein each cavity of each composite recess is adjacent the cavities of the other composite recess.

4. A face mask as defined in claim 3, wherein each cavity of each composite recess is separated from the each cavity of the other composite recess by a ridge.

5. A face mask as defined in claim 1, wherein the composite recesses intersect each other such that the digit cavities are bilaterally positioned relative to each other and the thenar eminence cavities are bilaterally positioned relative to each other.

6. A face mask as defined in claim 1, wherein the connection port is disposed between the digit cavities such that the connection port is aligned with the central axis ($A_{central}$) of the face mask.

7. A face mask as defined in claim 1, wherein each composite recess has a proximal end located at the thenar eminence cavity and a distal end located at the digit cavity, the proximal end being located lower than the distal end relative to a plane defined by the deformable rim.

8. A face mask as defined in claim 1, wherein the thenar eminence cavities each have one or more protruding ribs.

9. A face mask as defined in claim 1, wherein the dome includes a protuberance located between the thenar eminence cavities.

10. A face mask as defined in claim 9, wherein the thenar eminence cavities are separated by a ridge and wherein the protuberance extends upwardly from the ridge at one end of the ridge.

11. A face mask as defined in claim 9, wherein the digit cavities are separated by a ridge and wherein the protuberance is located lower than the ridge relative to a plane defined by the deformable rim.

12. A face mask as defined in claim 1, wherein the crossed composite recesses are positioned and contoured such that a user's thumb of one hand can be placed into one of the composite recesses, and such that the user's thumb of the other hand can be placed into the other composite recess, whereby the face mask allows for ambidextrous use.

13. A face mask as defined in claim 1, wherein the face mask is bilaterally symmetrical.

14. A face mask as defined in claim 1, further comprising an adapter attached to the connection port, the adapter including a ventilation port and an intubation port.

15. A face mask as defined in claim 14, wherein the intubation port and connection port extend along a common axis, and wherein the ventilation port extends along an angled axis relative to the common axis.

16. A face mask as defined in claim 14, wherein the adapter is removable.

17. A face mask kit comprising a face mask as defined in claim 1 and an adapter attachable to the connection port of the face mask, the adapter having an intubation port and a ventilation port.

18. A face mask, comprising:
    a deformable rim for engaging and forming a seal between the rim and a patient's face when the rim is pressed against the patients face in position over the mouth and nose;
    a dome connected to the rim and forming an enclosed air space when the rim is in position over the mouth and nose, the dome having a connection port and a contoured outer surface adjacent the connection port, the contoured outer surface having a pair of crossed composite recesses that intersect each other along a central axis ($A_{central}$) that passes through a central region of the dome; and
    an adapter having an intubation port and a ventilation port, wherein the adapter attaches to the connection port of the face mask such that the connection port and the intubation port of the adapter extend along a common axis and wherein the ventilation port extends along an angled axis relative to the common axis.

19. A face mask as defined in claim 18, wherein the common axis is aligned with a central portion of the patient's mouth when the rim is in position over the mouth and nose.

20. A face mask as defined in claim 18, wherein the adapter includes a sealing sleeve that attaches to the intubation port of the adapter such that it is aligned with the common axis for accommodating a fiber-optic scope, an endotracheal tube, or both a fiber-optic scope and an endotracheal tube.

21. A face mask as defined in claim 18, wherein the adapter includes a closure for the intubation port to prevent airflow through the intubation port when the intubation port is not in use.

22. A face mask as defined in claim 18, wherein the adapter is removable.

* * * * *